United States Patent [19]

Koshihara et al.

[11] Patent Number: 4,988,210

[45] Date of Patent: *Jan. 29, 1991

[54] METHOD AND APPARATUS FOR DETECTING DEFECTIVE PORTION ON OUTER SURFACE OF PIPE

[75] Inventors: Toshio Koshihara; Koji Ishihara; Toru Hirashima; Shunichiro Ishida; Haruhito Okamoto; Yuji Matoba, all of Tokyo, Japan

[73] Assignee: NKK Corporation, Tokyo, Japan

[*] Notice: The portion of the term of this patent subsequent to Oct. 10, 2006 has been disclaimed.

[21] Appl. No.: 319,977

[22] Filed: Mar. 7, 1989

[30] Foreign Application Priority Data

Mar. 18, 1988 [JP] Japan ................. 63-64819

[51] Int. Cl.$^5$ ............... G01N 25/72; G01M 3/00
[52] U.S. Cl. ........................... 374/5; 250/341; 374/124; 374/136; 392/407
[58] Field of Search .............. 374/5, 4, 57, 124; 73/40.5 R; 219/201, 342

[56] References Cited

U.S. PATENT DOCUMENTS

| | | | |
|---|---|---|---|
| 3,162,505 | 12/1964 | Hall | 73/40.5 R X |
| 3,164,988 | 1/1965 | Cook | 73/154 |
| 3,483,734 | 12/1969 | Wood | 73/40.5 R |
| 3,508,433 | 4/1970 | Bustin | 73/40.5 A |
| 3,656,344 | 4/1972 | Johns | 73/154 |
| 3,771,350 | 11/1973 | Romans | 73/40.5 R |
| 4,142,713 | 3/1979 | Nakasugi et al. | 374/4 X |
| 4,322,620 | 3/1982 | Steinhage | 374/124 X |
| 4,480,928 | 11/1984 | Halsor et al. | 374/57 |
| 4,854,724 | 8/1989 | Adams et al. | 374/5 |
| 4,872,762 | 10/1989 | Koshihara et al. | 374/5 |
| 4,884,456 | 12/1989 | Meline et al. | 73/826 X |
| 4,886,370 | 12/1989 | Koshihara et al. | 374/5 |

Primary Examiner—Daniel M. Yasich
Attorney, Agent, or Firm—Frishauf, Holtz, Goodman & Woodward

[57] ABSTRACT

A method and apparatus for detecting a defective portion on the outer surface not exposed of a pipe, which comprises: heating or cooling a pipe, the outer surface of which is not exposed, from the side of the inner surface thereof so that a difference in temperature is produced between a portion of the inner surface of the pipe corresponding to an accumulation of foreign matters or a thinner portion as a defective portion on the outer surface not exposed of the pipe and a portion of the inner surface of the pipe corresponding to a normal portion of the outer surface of the pipe; then shooting the inner surface of the pipe by means of a thermal imaging system while the difference in temperature still remains on the inner surface of the pipe to obtain a thermal image of the difference in temperature; and detecting the accumulation of foreign matters or the thinner portion as the defective portion on the outer surface of the pipe by means of the thus obtained thermal image.

14 Claims, 3 Drawing Sheets

METHOD AND APPARATUS FOR DETECTING DEFECTIVE PORTION ON OUTER SURFACE OF PIPE

FIELD OF THE INVENTION

The present invention relates to a method and an apparatus for detecting a defective portion existing on the outer surface not exposed of a pipe.

BACKGROUND OF THE INVENTION

On the outer surface not exposed of a pipe installed under the ground for transporting, for example, a fluid such as a gas or a liquid, a defective portion such as those listed below may be produced:

(1) An accumulation of foreign matters caused by the production of rust; and (2) A thinner portion caused by corrosion and the like.

Presence of an accumulation of foreign matters as mentioned above caused by the production of rust on the outer surface of a pipe causes such problems as reduction of the pipe wall thickness because of an extreme brittleness of the accumulation and easy peeloff from the pipe, finally producing a hole in the portion of the accumulation of foreign matters of the pipe. Presence of a thinner portion as mentioned above on the outer surface of the pipe results also in such problems as production of a hole in the portion having the thinner portion of the pipe. It is necessary therefore to promptly detect the above-mentioned defective portion on the outer surface of the pipe, and replace the pipe having such a defective portion with new one.

As a method for detecting a defective portion on the outer surface not exposed of a pipe, a method using ultrasonic waves is known, which comprises: transmitting ultrasonic waves toward the inner surface of a pipe to be tested in the interior of the pipe, receiving reflected waves of the transmitted ultrasonic waves, measuring the time required up to receiving the reflected waves, and detecting a defective portion on the outer surface of the pipe by means of the time required up to receiving the reflected waves.

However, the above-mentioned method using ultrasonic waves has the following problems:

(a) An error is often contained in the result of detection of a defective portion, thus preventing accurate detection.

(b) The range of a single run of detection, being only a point, is very narrow. It thus requires much time and labor for the detecting operation, leading to a low operating efficiency.

Under such circumstances, there is a strong demand for the development of a method and an apparatus which permit certain, easy and efficient detection of an accumulation of foreign matters or a thinner portion as a defective portion on the outer surface not exposed of a pipe, but a method and an apparatus provided with such properties have not as yet been proposed.

SUMMARY OF THE INVENTION

An object of the present invention is therefore to provide a method and an apparatus which permit certain, easy and efficient detection of an accumulation of foreign matters or a thinner portion as a defective portion on the outer surface not exposed of a pipe.

In accordance with one of the features of the present invention, there is provided a method for detecting a defective portion on the outer surface not exposed of a pipe, characterized by:

heating or cooling a pipe from the side of the inner surface thereof so that a difference in temperature is produced between a portion of the inner surface of said pipe corresponding to a defective portion on the outer surface not exposed of said pipe and a portion of the inner surface of said pipe corresponding to a normal portion of the outer surface of said pipe; then shooting the inner surface of said pipe by means of a thermal imaging system while said difference in temperature still remains on the inner surface of said pipe to obtain a thermal image of said difference in temperature; and detecting said defective portion on the outer surface of said pipe by means of the thus obtained thermal image.

DETAILED DESCRIPTION OF PREFERRED EMBODIMENTS

From the above-mentioned point of view, extensive studies were carried out to develop a method and an apparatus which permit certain, easy and efficient detection of an accumulation of foreign matters or a thinner portion as a defective portion on the outer surface not exposed of a pipe. As a result, the following finding was obtained.

For example, a pipe having an outer surface not exposed is heated or cooled for a certain period of time from the side of the inner surface thereof. If there is an accumulation of foreign matters as a defective portion on the outer surface of the pipe, this accumulation of foreign matters has a lower thermal conductivity than that of a normal portion of the pipe. If there is a thinner portion as a defective portion on the outer surface of the pipe, on the other hand, this thinner portion has a smaller thermal capacity than that of a normal portion of the pipe. A difference in temperature is therefore produced between a portion of the inner surface of the pipe corresponding to the defective portion on the outer surface thereof, on the one hand, and a portion of the inner surface of the pipe corresponding to the normal portion of the outer surface of the pipe, on the other hand. By shooting the inner surface of the pipe by means of a thermal imaging system while this difference in temperature still remains on the inner surface of the pipe to obtain a thermal image of the above-mentioned difference in temperature, it is possible to detect the defective portion on the outer surface not exposed of the pipe by means of the thus obtained thermal image.

The present invention was developed on the basis of the aforementioned finding. Now, the method and the apparatus for detecting a defective portion on the outer surface not exposed of a pipe of the present invention are described with reference to drawings.

Figure 1:
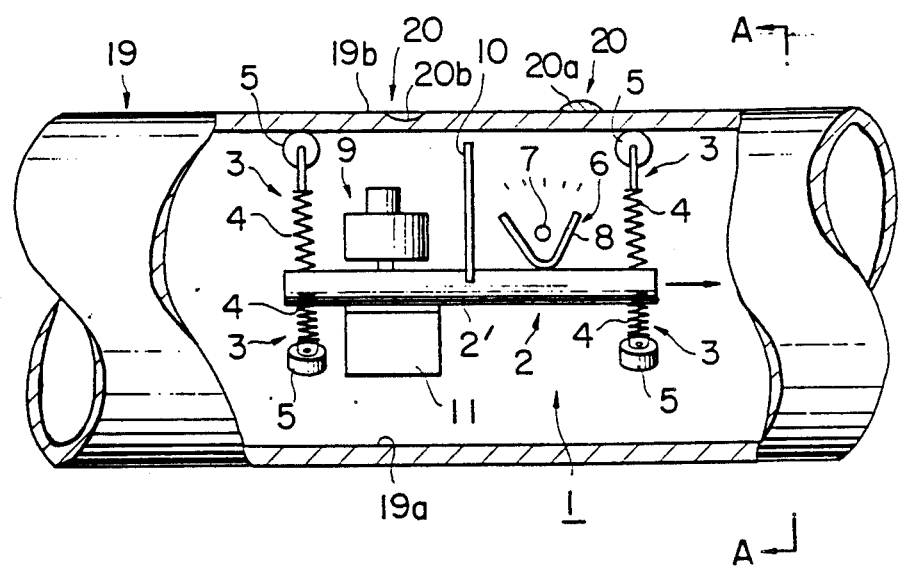
FIG. 1 is a schematic descriptive side view illustrating a first embodiment of the apparatus of the present invention for detecting a defective portion on the outer surface not exposed of a pipe, arranged in the pipe.
Figure 2:
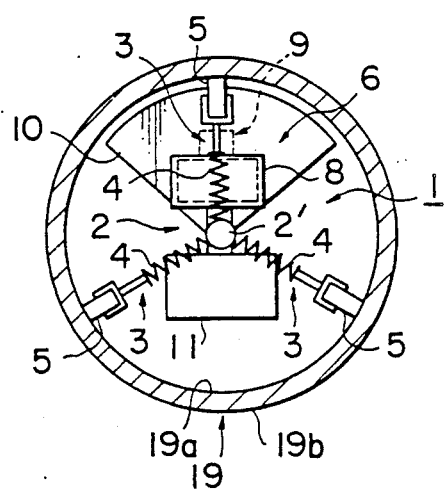
FIG. 2 is a sectional view of FIG. 1 cut along the line A—A.

FIG. 1 is a schematic descriptive side view illustrating a first embodiment of the apparatus of the present invention, and FIG. 2 is a sectional view of FIG. 1 cut along the line A—A. As shown in FIGS. 1 and 2, the apparatus 1 according to the first embodiment of the present invention for detecting a defective portion on the outer surface not exposed of a pipe comprises a pig 2 travellable through a pipe 19, the outer surface 19b of which is not exposed, in the axial direction of the pipe 19, and other components mounted on the pig 2, i.e., a temperature change imparting means 6, a thermal imaging system 9, an infrared ray shielding plate 10 and a means 11 for storing a thermal image obtained by means of the thermal imaging system 9.

The pig 2 comprises a pig body 2' capable of mounting the temperature change imparting means 6, the thermal imaging system 9, the infrared ray shielding plate 10 and the storing means 11, a plurality of supporting arms 3 each comprising a spring 4, radially arranged at equal intervals in the circumferential direction of the pipe 19 on the leading end portion and the trailing end portion of the pig body 2', and rollers 5 in contact with the inner surface 19a of the pipe 19, each rotatably fitted to the tip of each of the supporting arms 3. The plurality of supporting arms 3 elastically support the pig body 2' so that the center axis of the pig body 2' substantially agrees with the center axis of the pipe 19 when the pig body 2' travels through the pipe 19 in the axial direction thereof.

The temperature change imparting means 6 comprises a heating mechanism including a reflecting plate 8 having a V-shaped section and a bar-shaped infrared heater 7 arranged in the reflecting plate 8. The temperature change imparting means 6 is mounted on the upper surface of the pig body 2' at a leading portion thereof relative to the travelling direction of the pig 2 and toward the inner surface 19a of the pipe 19. The temperature change imparting means 6 thus mounted on the pig 2 heats the pipe 19 from the side of the inner surface 19a thereof so that a differences in temperature is produced between a portion of the inner surface 19a of the pipe 19 corresponding to a defective portion 20 on the outer surface 19b not exposed of the pipe 19 and a portion of the inner surface 19a of the pipe 19 corresponding to a normal portion of the outer surface 19b of the pipe 19.

The thermal imaging system 9 is mounted on the upper surface of the pig body 2' at a position behind the temperature change imparting means 6 relative to the travelling direction of the pig 2 and toward the inner surface 19a of the pipe 19. The temperature change imparting means 6 and the thermal imaging system 9 are arranged on the same plane containing the center axis of the pipe 19. The thermal imaging system 9 thus mounted on the pig 2 shoots the inner surface 19a heated by the above-mentioned temperature change imparting means 6 to obtain a thermal image of the inner surface 19a.

The infrared ray shielding plate 10 is formed into a fan shape with an aluminum alloy plate and is fitted to the pig body 2' between the temperature change imparting means 6 and the thermal imaging system 9 so as to prevent infrared rays emitted from the temperature change imparting means 6 from coming into the thermal imaging system 9. The infrared ray shielding plate 10 may be made of any material having a thermal resistance and a property to shield infrared rays, and any of various metals other than aluminum alloy, synthetic resin and synthetic rubber may be used as a material for the infrared ray shielding plate 10.

The storing means 11 is fitted to the pig body 2, and receives a thermal image signal from the thermal imaging system 9 and stores same.

According to the above-mentioned apparatus 1 of the first embodiment of the present invention, a defective portion 20 existing on the outer surface 19b not exposed of the pipe 19 is detected as follows.

The apparatus 1 of the first embodiment of the present invention is inserted, as shown in FIGS. 1 and 2, into the pipe 19 from an open end thereof, so that the center axis of the pig body 2' substantially agrees with the center axis of the pipe 19. The pig 2 of the above-mentioned apparatus 1 thus inserted into the pipe 19 is connected through a rope (not shown) to a rope winder (not shown) provided outside the other open end of the pipe 19. By winding up the rope by means of the rope winder, the pig 2 travels at a prescribed speed through the pipe 19 in the axial direction thereof.

During travel of the pig 2 through the pipe 19, the temperature change imparting means 6 mounted on the pig 2 heats the pipe 19 from the side of the inner surface 19a thereof so that a difference in temperature is produced between a portion of the inner surface 19a of the pipe 19 corresponding to the defective portion 20 on the outer surface 19b of the pipe 19 and a portion of the inner surface 19a of the pipe 19 corresponding to the normal portion of the outer surface 19b of the pipe 19. More specifically, the temperature change imparting means 6 mounted on the pig 2 travelling through the pipe 19 continuously heats the pipe 19 from the side of the inner surface 19a thereof in the axial direction thereof over a prescribed width in the circumferential direction of the pipe 19.

During travel of the pig 2 through the pipe 19, the thermal imaging system 9 mounted on the pig 2 together with the temperature change imparting means 6, shoots the inner surface 19a of the pipe 19 thus heated as described above by means of the temperature change imparting means 6 to obtain a thermal image thereof, while the above-mentioned difference in temperature still remains on the inner surface 19a of the pipe 19 between the portion of the inner surface 19a of the pipe 19 corresponding to the defective portion on the outer surface 19b of the pipe 19, on the one hand, and the portion of the inner surface 19a of the pipe 19 corresponding to the normal portion of the outer surface 19b of the pipe 19, on the other hand. More particularly, the thermal imaging system 9 mounted on the pig 2 travelling through the pipe 19 continuously shoots the inner surface 19a of the pipe 19 in the axial direction thereof over a prescribed width in the circumferential direction thereof to obtain a thermal image of the inner surface 19a of the pipe 1, immediately after the heating of the pipe 19 by means of the temperature change imparting means 6.

The storing means 11 mounted on the pig 2 travelling through the pipe 19 continuously receives a thermal image signal from the above-mentioned thermal imaging system 9 and stores same.

The thermal image signal thus stored in the storing means 11 is regenerated by a regenerating means (not shown), and the obtained thermal image of the inner surface 19a of the pipe 19 is displayed on a monitor TV screen (not shown). It is thus possible to detect the defective portion existing on a portion of the outer surface 19b of the pipe 19 in the axial direction thereof, by means of the above-mentioned thermal image.

In the case where an accumulation of foreign matters 20a as the defective portion 20 is present on the outer surface 19b of the pipe 19, a thermal conductivity of the accumulation of foreign matters 20a on the pipe 19 is lower than that of the normal portion of the pipe 19. Therefore, because of the presence of the accumulation of foreign matters 20a having a lower thermal conductivity, the temperature of the portion of the inner surface 19a of the pipe 19 corresponding to the accumulation of foreign matters 20a on the outer surface 19b of the pipe 19 increases more slowly than the temperature of the portion of the inner surface 19a of the pipe 19 corresponding to the normal portion of the outer surface 19b of the pipe 19 under the effect of heating by means of the temperature change imparting means 6. As a result, after heating for a certain period of time by means of the temperature change imparting means 6, the temperature of the portion of the inner surface 19a of the pipe 19 corresponding to the accumulation of foreign matters 20a on the outer surface 19b of the pipe 19 becomes lower than the temperature of the portion of the inner surface 19a of the pipe 19 corresponding to the normal portion of the outer surface 19b of the pipe 19. It is therefore possible to detect a position, a shape and an approximate thickness of the accumulation of foreign matters 20a as the defective portion 20 on the outer surface 19b of the pipe 19 by means of the portion showing a lower temperature in the thermal image obtained as described above.

In the case where a thinner portion 20b as the defective portion 20 is present on the outer surface 19b of the pipe 19, a thermal capacity of the thinner portion 20b on the pipe 19 is smaller than that of the normal portion of the pipe 19. Therefore, the temperature of the portion of the inner surface 19a of the pipe 19 corresponding to the thinner portion 20b on the outer surface 19b of the pipe 19 increases more rapidly than the temperature of the portion of the inner surface 19a of the pipe 19 corresponding to the normal portion of the outer surface 19b of the pipe 19 under the effect of heating by means of the temperature change imparting means 6. As a result, after heating for a certain period of time by means of the temperature change imparting means 6, the temperature of the portion of the inner surface 19a of the pipe 19 corresponding to the thinner portion 20b on the outer surface 19b of the pipe 19 becomes higher than the temperature of the portion of the inner surface 19a of the pipe 19 corresponding to the normal portion of the outer surface 19b of the pipe 19. Therefore, it is possible to detect a position, a shape and an approximate depth of the thinner portion 20b as the defective portion 20 on the outer surface 19b of the pipe 19 by means of the portion showing a higher temperature in the thermal image obtained as described above.

According to the apparatus 1 of the first embodiment of the present invention, the defective portion 20 existing in a portion of the outer surface 19b of the pipe 19 is detected in the axial direction thereof over a prescribed width in the circumferential direction of the pipe 19 by means of the thermal image obtained a described above.

In order to detect the defective portion 20 on the outer surface 19b of the pipe 19 over the entire circumference thereof, it suffices, after conducting detection in the axial direction of the pipe 19 as described above, to set the apparatus 1 of the first embodiment of the present invention at a position moved by a prescribed angle in the circumferential direction of the pipe 19, conduct a detection similar to that described above, and repeating this operation a plurality of times.

Now, a second embodiment of the apparatus of the present invention is described with reference to FIGS. 3 and 4.

Figure 3:
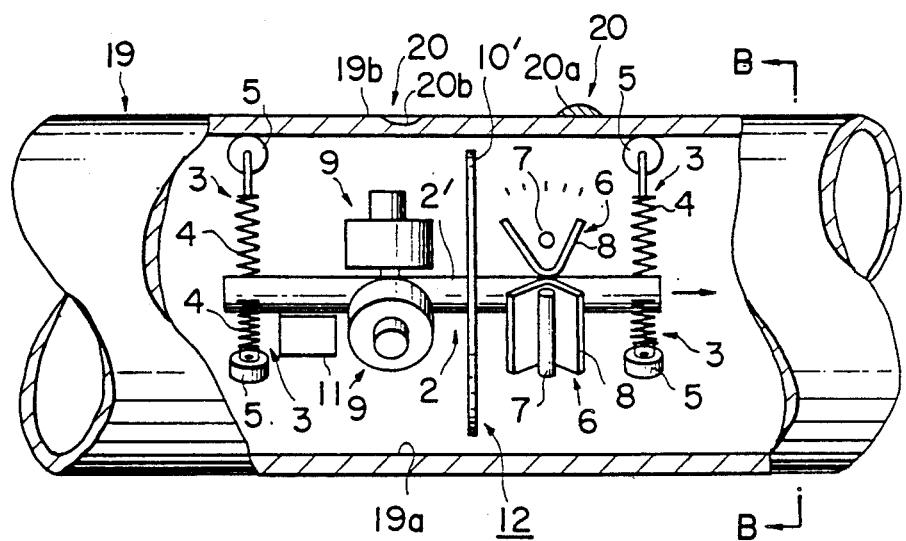
FIG. 3 is a schematic descriptive side view illustrating a second embodiment of the apparatus of the present invention for detecting a defective portion on the outer surface not exposed of a pipe, arranged in the pipe.
Figure 4:
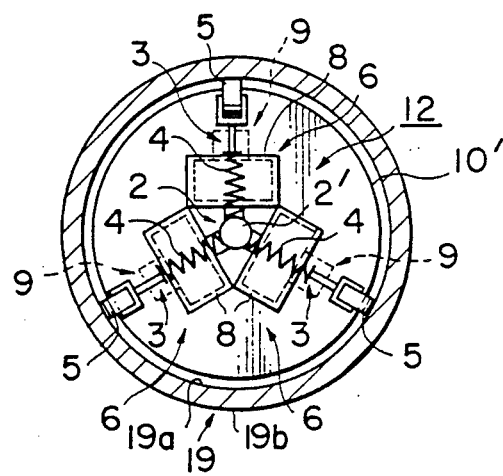
FIG. 4 is a sectional view of FIG. 3 cut along the line B—B.

FIG. 3 is a schematic descriptive side view illustrating a second embodiment of the apparatus of the present invention, and FIG. 4 is a sectional view of FIG. 3 cut along the line B—B. As shown in FIGS. 3 and 4, the apparatus 12 according to the second embodiment of the present invention for detecting a defective portion on the outer surface not exposed of a pipe comprises a pig 2a travellable through a pipe 19, the outer surface 19b of which is not exposed, in the axial direction of the pipe 19, and other components mounted on the pig 2a, .e., a plurality of temperature change imparting means 6a, a plurality of thermal imaging systems 9a in a number equal to that of the plurality of temperature change imparting means 6a, an infrared ray shielding plate 10a and a means 11a for independently storing individual thermal images obtained by means of the plurality of thermal imaging systems 9a.

Since the construction of the apparatus 12 of the second embodiment of the present invention is identical with that of the apparatus 1 of the above-mentioned first embodiment of the present invention except for the following points, the same reference numerals are assigned to the corresponding components, and description thereof is omitted:

(1) the plurality of temperature change imparting means 6a are mounted on the pig body 2a of the pig 2;

(2) the plurality of thermal imaging systems 9a in the number equal to that of the plurality of temperature change imparting means 6a are mounted on the pig body 2a of the pig 2a;

(3) the infrared ray shielding plate 10a has a circular shape; and (4) the single storing means 10a can independently store individual thermal images obtained by means of the plurality of thermal imaging systems 9a.

The plurality of temperature change imparting means 6a, mounted on the pig body 2a at a leading portion thereof, relative to the travelling direction of the pig 2a are arranged at equal intervals in the circumferential direction of the pipe 19 and toward the inner surface 19a of the pipe 19. The plurality of temperature change imparting means 6a heat the pipe 19 from the side of the inner surface 19a thereof over the entire circumference thereof.

The plurality of thermal imaging systems 9a in the number equal to that of the above-mentioned plurality of temperature change imparting means 6a are mounted on the pig body 2a at positions behind the plurality of temperature change imparting means 6a relative to the travelling direction of the pig 2a. Each pair of temperature change imparting means 6a and the thermal imaging system 9a are arranged on the same plane containing the center axis of the pipe 19. The plurality of thermal imaging systems 9a shoot the inner surface 19a of the pipe 19, which has been heated over the entire circumference thereof by the plurality of temperature change imparting means 6a, over the entire circumference of the inner surface 19a of the pipe 19 to obtain the thermal images thereof.

The infrared ray shielding plate 10a has a circular shape, and is fitted to the pig body 2a between the temperature change imparting means 6 and the thermal imaging systems 9a so as to prevent infrared rays emitted from the temperature change imparting means 6a from coming into the thermal imaging systems 9.

The single storing means 11a independently receives the individual thermal image signals from the plurality of thermal imaging systems 9 and stores same. Storing means in a number equal to that of the plurality of thermal imaging systems 9a may be independently provided without using such a single storing means 11a.

Since, according to the above-mentioned apparatus 12 of the second embodiment of the present invention, the defective portion 20 existing on the outer surface 19b not exposed of the pipe 19 is detected in the same manner as in the above-mentioned apparatus 1 of the first embodiment of the present invention, description of the manner of application thereof is omitted. According to the apparatus 12 of the second embodiment of the present invention, the plurality of thermal imaging systems 9a shoot the inner surface 19a of the pipe 19, which has bene heated over the entire circumference thereof by the plurality of temperature change imparting means 6a, over the entire circumference of the inner surface 19a of the pipe 19 to obtain the thermal images thereof. Therefore, the defective portion 20 on the outer surface 19a of the pipe 19 can be detected over the entire circumference of the pipe 19 by only causing this apparatus 12 to make a single travel through the pipe 19.

Now, a third embodiment of the apparatus of the present invention is described with reference to FIGS. 5 and 6.

Figure 5:
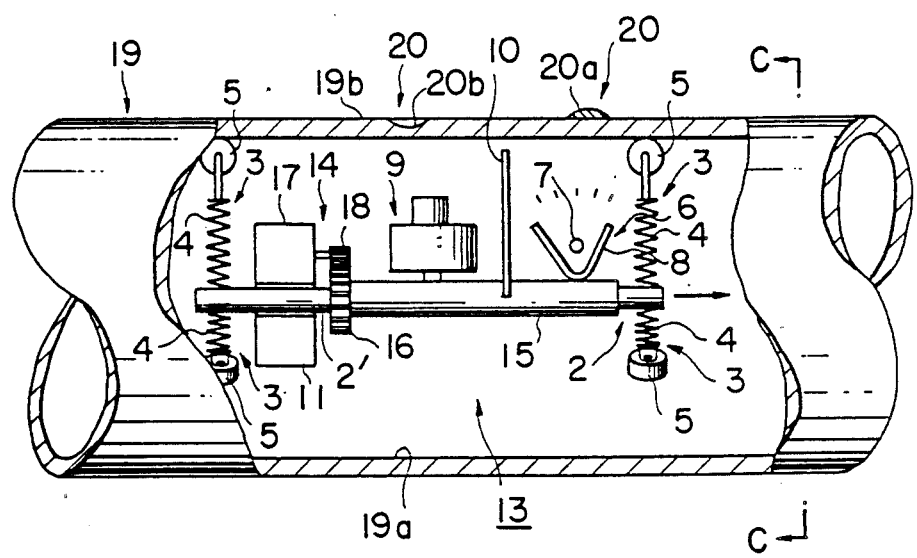
FIG. 5 is a schematic descriptive side view illustrating a third embodiment of the apparatus of the present invention for detecting a defective portion on the outer surface not exposed of a pipe, arranged in the pipe.
Figure 6:
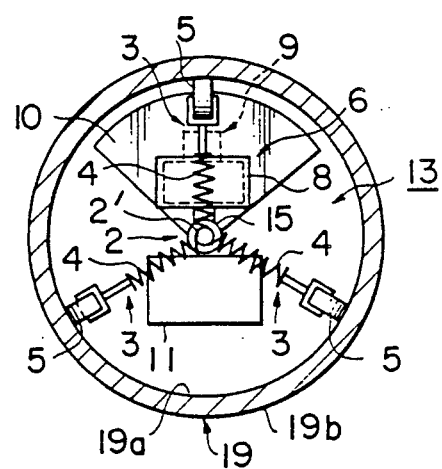
FIG. 6 is a sectional view of FIG. 5 cut along the line C—C.

FIG. 5 is a schematic descriptive side view illustrating a third embodiment of the apparatus of the present invention, and FIG. 6 is a sectional view of FIG. 5 cut along the line C—C. As shown in FIGS. 5 and 6, the apparatus 13 according to the third embodiment of the present invention for detecting a defective portion on the outer surface not exposed of a pipe basically comprises a pig 2b travellable through a pipe 19, the outer surface 19b of which is not exposed, in the axial direction of the pipe 19, and other components mounted on the pig 2b, i.e., a temperature change imparting means 6b, a thermal imaging system 9b, an infrared ray shielding plate 10b and a means 11b for storing a thermal image obtained by means of the thermal imaging system 9b, and the apparatus 13 further includes a driving mechanism 14 for rotating the temperature change imparting means 6b, the thermal imaging system 9b and the infrared ray shielding plate 10b around the center axis of the pig 2b.

Since the construction of the apparatus 13 of the third embodiment of the present invention is identical with that of the apparatus 1 of the above-mentioned first embodiment of the present invention except that the driving mechanism 14 for rotating the temperature change imparting means 6b, the thermal imaging system 9b and the infrared ray shielding plate 10b around the center axis of the pig 2b is added, the same reference numerals are assigned to the corresponding components, and description thereof is omitted.

The driving mechanism 14 comprises a sleeve 15 concentrically and rotatably engaged to the pig body 2b and having a length shorter than that of the pig body 2b, a gear 16 fixed to the trailing end portion of the sleeve 15 relative to the travelling direction of the pig 2b, a pinion 18 engaging with the gear 16, and a motor 17, fitted to the pig body 2b, for rotating the pinion 18.

The temperature change imparting means 6b, the thermal imaging system 9b and the infrared ray shielding plate 10b are fitted to the above-mentioned sleeve 15 of the driving mechanism 14. More specifically, the temperature change imparting means 6b is fitted to the sleeve 15 at a leading portion thereof relative to the travelling direction of the pig 2b and toward the inner surface 19a of the pipe 19. The thermal imaging system 9b is fitted to the sleeve 15 at a position behind the temperature change imparting means 6b relative to the travelling direction of the pig 2b and toward the inner surface 19a of the pipe 19. The temperature change imparting means 6b and the thermal imaging system 9b are arranged in the same plane containing the center axis of the pipe 19. The infrared ray shielding plate 10b is also fitted to the sleeve 15 between the temperature change imparting means 6b and the thermal imaging system 9b.

Therefore, the motor 17 of the driving mechanism 14 rotates the pinion 18 to cause the sleeve 15 to rotate around the pig body 2b' in cooperation with the gear 16, whereby the temperature change imparting means 6b, the thermal imaging system 9b and the infrared ray shielding plate 10 rotate round the pig body 2b.

According to the above-mentioned apparatus 13 of the third embodiment of the present invention, the defective portion 20 existing on the outer surface 19b not exposed of the pipe 19 is detected as follows.

The pig 2b of the apparatus 13 of the third embodiment of the present invention also travels at a prescribed speed through the pipe 19 in the axial direction thereof by using a rope winder (not shown) as in the apparatus 1 of the above-mentioned first embodiment of the present invention.

During travel of the pig 2b through the pipe 19, the temperature change imparting means 6b, the thermal imaging system 9b and the infrared ray shielding plate 10 rotate at a prescribed speed around the pig body 2'.

More specifically, during travel of the pig 2b through the pipe 19, the temperature change imparting means 6b, which rotates around the pig body 2', heats the pipe 19 from the side of the inner surface 19a thereof so that a difference in temperature is produced between the portion of the inner surface 19a of the pipe 19 corresponding to the defective portion 20 on the outer surface 19b of the pipe 19 and the portion of the inner surface 19a of the pipe 19 corresponding to the normal portion of the outer surface 19b of the pipe 19. More particularly, the above-mentioned temperature change imparting means 6b spirally and continuously heats the pipe 19 from the side of the inner surface 19a thereof over the entire circumference with a prescribed width in the axial direction of the pipe 19.

On the other hand, during travel of the pin 2b through the pipe 19, the thermal imaging system 9b, which rotates together with the temperature change imparting means 6b around the pig body 2b', shoots the inner surface 19a of the pipe 19 thus heated as described above by means of the temperature change imparting means 6b to obtain a thermal image thereof, while the above-mentioned difference in temperature still remains on the inner surface 19a of the pipe 19 between the portion of the inner surface 19a of the pipe 19 corresponding to the defective portion 20 on the outer surface 19b of the pipe 19, on the one hand, and the portion of the inner surface 19a of the pipe 19 corresponding to the normal portion of the outer surface 19b of the pipe 19, on the other hand. More specifically, the above-mentioned thermal imaging system 9b spirally and continuously shoots the inner surface 19a of the pipe 19 over the entire circumference with a prescribed with in the axial direction of the pipe 19 to obtain a thermal image of the inner surface 19a of the pipe 19, immediately after the heating of the pipe 19 by means of the temperature change imparting means 6b.

The storing means 11b mounted on the pipe 2b travelling through the pipe 19 continuously receives a thermal image signal from the above-mentioned thermal imaging system 9b and stores same.

The thermal image signal thus stored in the storing means 11b is regenerated by a regenerating means (not shown), and the obtained thermal image of the inner surface 19a of the pipe 19 is displayed on a monitor TV screen (not shown). It is therefore possible to detect the defective portion 20 on the outer surface 19a of the pipe 19 over the entire circumference of the pipe 19 by means of the above-mentioned thermal image. More particularly, as in the apparatus 1 of the above-mentioned first embodiment of the present invention, it is possible to detect a position, a shape and an approximate thickness of the accumulation of foreign matters 20a as the defective portion 20 on the outer surface 19b of the pipe 19, and a position, a shape and an approximate depth of a thinner portion 20b as the defective portion on the outer surface 19b of the pipe 19, by means of the obtained thermal image. According to the apparatus 13 of the third embodiment of the present invention, during travel of the pig 26 through the pipe 19, the temperature change imparting means 6 and the thermal imaging system 9b are rotated by the driving mechanism 14 around the pig body 2b', and as a result, the temperature change imparting means 6b spirally and continuously heats the pipe 19 from the side of the inner surface 19a thereof over the entire circumference thereof, and the thermal imaging system 9b spirally and continuously shoots the inner surface 19a of the thus heated pipe 19, over the entire circumference thereof, to obtain a thermal image thereof. It is not therefore necessary to provide a plurality of temperature change imparting means 6b and a plurality of thermal imaging systems 9b, and it is possible to detect the defective portion 20 on the outer surface 19b of the pipe 19 over the entire circumference thereof by only causing this apparatus 13 to make a single travel through the pipe 19.

In the apparatuses 1, 12 and 13 of the above-mentioned first to third embodiments of the present invention, the thermal image signal from the thermal imaging system 9b may be processed by an image processor (not shown), as required, and the thermal image signal thus processed may be entered into the storing means 11, 11a, 11b or the thermal image signal represented by the regenerating means may be processed by the above-mentioned image processor, and the thermal image signal thus processed may be entered into the monitor TV.

In the apparatuses 1, 12 and 13 of the above-mentioned first to third embodiments of the present invention, the sorting means 11, 11a, 11b is mounted on the pig 2. However, the storing means 11 may be arranged outside the pipe 19, for example, near the rope winder for causing the pig 2, 2a, 2b to travel, and the storing means 11 and the thermal imaging system 9, 9a, 9b mounted on the pig 2 may be connected by a cable.

In the apparatuses 1, 12 and 13 of the above-mentioned first to third embodiments of the present invention, the pig 2, 2a, 2b travels through the pipe 19 by the action of the rope winder. However, the pig 2, 2a, 2b may be equipped with a travelling mechanism for its own travel.

In the apparatuses 1, 12 and 13 of the above-mentioned first to third embodiments of the present invention, the temperature change imparting means 6, 6a, 6b comprises the heating mechanism including the infrared heater 7, 7a, 7b. However, any heating mechanism having the function of heating the pipe 19 from the side of the inner surface 19a thereof may be used: for example, a bag filled with hot water and excellent in liquid-tightness and wear resistance may be used as the above-mentioned temperature change imparting means 6, 6a, 6b. In this case, the above-mentioned bag is mounted on the pig 2, 2a, 2b so as to be in contact with the inner surface 19a of the pipe 19. By using such a bag, it is possible to safely detect the defective portion 20 on the outer surface 19b of the pipe 19 even when a combustible gas is present in the pipe 19.

In the apparatuses 1, 12 and 13 of the above-mentioned first to third embodiments, a cooling mechanism as the temperature change imparting means 6, 6a, 6b may be used in place of the above-mentioned heating mechanism as the temperature change imparting means 6, 6a, 6b. As the cooling mechanism as the temperature change imparting means 6, 6a, 6b, a mechanism for ejecting a liquefied gas, a low-boiling-point liquid or the like onto the inner surface 19a of the pipe 19 is applicable. Furthermore, a bag filled with a low-temperature gas or liquid and excellent in liquid-tightness and wear resistance may be used as the above-mentioned temperature change imparting means 6, 6a, 6b. In this case, the above-mentioned bag is mounted on the pig 2, 2a, 2b so as to be in contact with the inner surface 19a of the pipe 19.

In the apparatuses 1, 12 and 13 of the first to third embodiment of the present invention, when the cooling mechanism as the temperature change imparting means 6, 6a, 6b is used in place of the heating mechanism as the temperature change imparting means 6, 6a, 6b, the defective portion 20 on the outer surface 19b of the pipe 19 is detected as follows.

In the case where an accumulation of foreign matters 20a as the defective portion 20 is present on the outer surface 19b of the pipe 19, a thermal conductivity of the accumulation of foreign matters 20a on the pipe 19 is lower than that of the normal portion of the pipe 19. Therefore, because of the presence of the accumulation of foreign matters 20a having a low thermal conductivity, the temperature of the portion of the inner surface 19a of the pipe 19 corresponding to the accumulation of foreign matters 20a on the outer surface 19b of the pipe 19 decreases more slowly than the temperature of the portion of the inner surface 19a of the pipe 19 corresponding to the normal portion of the outer surface 19b of the pipe 19 under the effect of cooling by means of the temperature change imparting means 6, 6a, 6b. As a result, after cooling for a certain period of time by means of the temperature change imparting means 6, 6a, 6b, the temperature of the portion of the inner surface 19a of the pipe 19 corresponding to the accumulation of foreign matters 20a on the outer surface 19b of the pipe 19 becomes higher than the temperature of the portion of the inner surface 19a of the pipe 19 corresponding to the normal portion of the outer surface 19b of the pipe 19. It is therefore possible to detect a position, a shape and an approximate thickness of the accumulation of foreign matters 20a as the defective portion 20 on the outer surface 19b of the pipe 19 by means of the portion showing a higher temperature in the thermal image obtained as described above.

In the case where a thinner portion 20b as the defective portion 20 is present on the outer surface 19b of the pipe 19, a thermal capacity of the thinner portion 20b on the pipe 19 is smaller than that of the normal portion of the pipe 19. Therefore, the temperature of the portion of the inner surface 19a of the pipe 19 corresponding to the thinner portion 20b on the outer surface 19b of the pipe 19 decreases more rapidly than the temperature of the portion of the inner surface 19a of the pipe 19 corresponding to the normal portion of the outer surface 19b of the pipe 19 under the effect of cooling by means of the temperature change imparting means 6, 6a, 6b. As a result, after cooling for a certain period of time by means of the temperature change imparting means 6, 6a, 6b, the temperature of the portion of the inner surface 19a of the pipe 19 corresponding to the thinner portion 20b on the outer surface 19b of the pipe 19 becomes lower than the temperature of the portion of the inner surface 19a of the pipe 19 corresponding to the normal portion of the outer surface 19b of the pipe 19. It is therefore possible to detect a position, a shape and an approximate depth of the thinner portion 20b as the defective portion 20 on the outer surface 19b of the pipe 19 by means of the portion showing a lower temperature in the thermal image obtained as described above.

In the apparatuses 1, 12 and 13 of the above-mentioned first to third embodiments of the present invention, the thermal imaging system 9, 9a, 9b is arranged behind the temperature change imparting means 6, 6a, 6b relative to the travelling direction of the pig 2, 2a, 2b. In the present invention, however the arrangement of the temperature change imparting means 6, 6a, 6b and the thermal imaging system 9, 9a, 9b is not limited to the above-mentioned one, but the temperature change imparting means 6, 6a, 6b and the thermal imaging system 9, 9a, 9b may be arranged along the circumferential direction of the pipe 19.

Furthermore, in the apparatuses 1, 12 and 13 of the above-mentioned first to third embodiments of the present invention, the thermal imaging system 9, 9a, 9b is directed toward the inner surface 19a of the pipe 19 and directly shoots the inner surface 19a of the pipe 19. However, the thermal imaging system 9 may be directed to the direction parallel to the travelling direction of the pig 2, 2a, 2b and indirectly shoot the inner surface 19a of the pipe 19 over the entire circumference thereof through a conical reflecting mirror which is arranged coaxially with the optical axis of the thermal imaging system 9, 9a, 9b and directed thereto. In this case, it is preferable to heat the inner surface 19a of the pipe 19 over the entire circumference thereof with the use of a heating mechanism as the temperature change imparting means 6, 6a, 6b which comprises a ring-shaped reflecting plate having a V-shaped section arranged concentrically with the pig body 2', 2a', 2b' and a ring-shaped infrared heater arranged in the ring-shaped reflecting plate.

Now, an example of the apparatus of the present invention is described.

EXAMPLE

Four circular thinner portions 20b having a diameter of 50 b mm and respective depths of 1 b mm, 2 b mm, 3 b mm and 4 b mm were formed on the outer surface 19b of a steel pipe 19 having an outer diameter of 160 mm and a wall thickness of 7 mm, along the axial direction of the pipe 19. These four circular thinner portions 20b as the defective portions 20 on the outer surface 19b of the pipe 19 were detected by means of the apparatuses 1, 12 and 13 of the above-mentioned first to third embodiments of the present invention. More particularly, the pipe 19 was heated from the side of the inner surface 19a thereof by means of the heating mechanism as the temperature change imparting means 6 so that a difference in temperature was produced between a portion of the inner surface 19a of the pipe 19 corresponding to the above-mentioned four thinner portions as the defective portions 20 on the outer surface 19b of the pipe 19, on the one hand, and a portion of the inner surface 19a of the pipe 19 corresponding to the normal portion of the outer surface 19b of the pipe 19, on the other hand. Then the inner surface 19a of the pipe 19 was shot by means of the thermal imaging system 9 while the above-mentioned difference in temperature still remained on the inner surface 19a of the pipe 19 to obtain a thermal image of the difference in temperature.

The thus obtained thermal image of the difference in temperature on the inner surface 19a of the pipe 19 displayed a portion showing a temperature corresponding to the thinner portion having a depth of 1 mm, a portion showing a temperature corresponding to the thinner portion having a depth of 2 mm, a portion showing a temperature corresponding to the thinner portion having a depth of 3 mm, and a portion showing a temperature corresponding to the thinner portion having a depth of 4 mm. The portion showing the temperature corresponding to the thinner portion having a depth of 1 mm was displayed in a color indicating a temperature higher than that of the portion of the inner surface 19a of the pipe 19 corresponding to the normal portion of the outer surface 19b of the pipe 19; the portion showing the temperature corresponding to the thinner portion having a depth of 2 mm was displayed in a color indicating a temperature higher than that of the portion showing the temperature corresponding to the thinner portion having a depth of 1 mm; the portion showing the temperature corresponding to the thinner portion having a depth of 3 mm was displayed in a color indicating a temperature higher than that of the portion showing the temperature corresponding to the thinner portion having a depth of 2 mm; and the portion showing the temperature corresponding to the thinner portion having a depth of 4 mm was displayed in a color indicating a temperature higher than that of the portion showing the temperature corresponding to the thinner portion having a depth of 3 mm. The portion showing the temperature corresponding to the thinner portion having a depth of 4 mm was first displayed in the thermal image, and then, the portion showing the temperature corresponding to the thinner portion having a depth of 3 mm, the portion showing the temperature corresponding to the thinner portion having a depth of 2 mm, and the portion showing the temperature corresponding to the thinner portion having a depth of 1 mm were sequentially displayed in this order in the thermal image. It was thus possible to detect a position, a shape and an approximate depth of the thinner portions on the outer surface 19b of the pipe 19, by means of the above-mentioned portions in the thermal image, which showed respective temperatures higher than that of the portion of the inner surface a of the pipe 19 corresponding to the normal portion of the outer surface 19b of the pipe 19.

According to the present invention, as described above in detail, it is possible to provide a method and an apparatus which permit certain, easy and efficient detection of an accumulation of foreign matters or a thinner portion as a defective portion on the outer surface not exposed of a pipe, thus providing industrially useful effects.

What is claimed is:

1. A method for detecting a defective portion on the outer surface not exposed of a pipe, comprising the steps of imparting a temperature change to a pipe from the side of the inner surface thereof so that a difference in temperature is produced between a portion of the inner surface of said pipe corresponding to a defective portion on the outer surface not exposed of said pipe and a portion of the inner surface of said pipe corresponding to a normal portion of the outer surface of said pipe; then shooting the inner surface of said pipe by means of a thermal imaging system while said difference in temperature still remains on the inner surface of said pipe to obtain a thermal image of said difference in temperature; and detecting said defective portion on the outer surface of said pipe by means of the thus obtained thermal image.

2. The method as claimed in claim 1, comprising the steps of imparting said temperature change by heating said pipe from the side of the inner surface thereof so that a difference in temperature is produced between a portion of the inner surface of said pipe corresponding to said defective portion on the outer surface of said pipe, on the one hand, and a portion of the inner surface of said pipe corresponding to said normal portion of the outer surface of said pipe, on the other hand; then obtaining said thermal image of said difference in temperature, which has a portion showing a lower temperature, corresponding to an accumulation of foreign matters as said defective portion on the outer surface of said pipe; and detecting said accumulation of foreign matters as said defective portion by means of said thermal image.

3. The method as claimed in claim 1, comprising the step of imparting said temperature change by said pipe from the side of the inner surface thereof so that a difference in temperature is produced between a portion of the inner surface of said pipe corresponding to said defective portion on the outer surface of said pipe, on the one hand, and a portion of the inner surface of said pipe corresponding to said normal portion of the outer surface of said pipe, on the one hand; then obtaining said thermal image of said difference in temperature, which has a portion showing a higher temperature, corresponding to a thinner portion as said defective portion on the outer surface of said pipe; and detecting said thinner portion as said defective portion by means of said thermal image.

4. The method as claimed in claim 1, comprising the steps of imparting said temperature change by cooling said pipe from the side of the inner surface thereof so that a difference in temperature is produced between a portion of the inner surface of said pipe corresponding to said defective portion on the outer surface of said pipe, on the one hand, and a portion of the inner surface of said pipe corresponding to said normal portion of the outer surface of said pipe, on the other hand; then obtaining said thermal image of said difference in temperature, which has a portion showing a higher temperature, corresponding to an accumulation of foreign matters as said defective portion on the outer surface of said pipe; and detecting said accumulation of foreign matters as said defective portion by means of said thermal image.

5. The method as claimed in claim 1, comprising the steps of imparting said temperature change by cooling said pipe from the side of the inner surface thereof so that a difference in temperature is produced between a portion of the inner surface of said pipe corresponding to said defective portion on the outer surface of said pipe, on the one hand, and a portion of the inner surface of said pipe corresponding to said normal portion of the outer surface of said pipe, on the other hand; then obtaining said thermal image of said difference in temperature, which has a portion showing a lower temperature, corresponding to a thinner portion as said defective portion on the outer surface of said pipe; and detecting said thinner portion as said defective portion by means of said thermal image.

6. The method as claimed in claim 1, wherein:

said temperature change imparting step comprises continuously heating said pipe in the axial direction thereof over a prescribed width in the circumferential direction of said pipe;

said shooting step comprises continuously shooting the inner surface of said pipe, heated by said temperature change imparting step, in the axial direction of said pipe over said prescribed width in the circumferential direction thereof; and said temperature change imparting step and said shooting step following said temperature change imparting step are carried out for every width of said prescribed width in the circumferential direction of said pipe, thereby detecting said defective portion on the outer surface of said pipe over the entire circumference thereof.

7. The method as claimed in claim 1, wherein:

said temperature change imparting step comprises continuously cooling said pipe in the axial direction thereof over a prescribed width in the circumferential direction of said said shooting step comprises continuously shooting the inner surface of said pipe, cooled by said temperature change imparting step, in the axial direction of said pipe over said prescribed width in the circumferential direction thereof; and said temperature change imparting step and said shooting step following said temperature change imparting step are carried out for every width of said prescribed width in the circumferential direction of said pipe, thereby detecting said defective portion on the outer surface of said pipe over the entire circumference thereof.

8. An apparatus for detecting a defective portion on the outer surface not exposed of a pipe, comprising:
- a pig travellable through a pipe, the outer surface of which is not exposed, in the axial direction of said pipe;
- at least one means, mounted on said pig, for imparting a temperature change to a portion of said pipe from the side of the inner surface thereof; and
- at least one thermal imaging system, mounted on said pig, for shooting said portion of the inner surface of said pipe to obtain a thermal image of the inner surface of said pipe.

9. The apparatus as claimed in claim 8, wherein:
- said at least one temperature change imparting means comprises a single temperature change imparting means; and
- said at least one thermal imaging system comprises a single thermal imaging system.

10. The apparatus as claimed in claim 8, wherein:
- said at least one temperature change imparting means comprises a plurality of temperature change imparting means, and said plurality of temperature change imparting means are arranged in the circumferential direction of said pipe at equal intervals;
- said at least one thermal imaging system comprises a plurality of thermal imaging systems in a number equal to that of said plurality of temperature change imparting means, and said plurality of thermal imaging systems are arranged behind said plurality of temperature change imparting means relative to the travelling direction of said pig; and
- each pair of said temperature change imparting means and said thermal imaging system are arranged on the same plane containing the center axis of said pipe.

11. The apparatus as claimed in claim 8, wherein:
- said apparatus contains a driving mechanism for rotating said at least one temperature change imparting means and said at least one thermal imaging system around the center axis of said pig.

12. The apparatus as claimed in claim 8, wherein:
- at least one infrared ray shielding plate means, for preventing infrared rays emitted from said at least one temperature change imparting means from coming into said at least one thermal imaging system, is provided between said at least one temperature change imparting means and said at least one thermal imaging system.

13. The apparatus as claimed in claim 8 wherein:
- said apparatus includes a means for storing said thermal image obtained by means of said at least one thermal imaging system.

14. The apparatus as claimed in claim 13, wherein:
- said means for storing said thermal image is mounted on said pig.

* * * * *